(12) United States Patent
Gertsenchtein (10) Patent No.: US 11,554,216 B2
(45) Date of Patent: Jan. 17, 2023

(54) SHIELDED SYRINGE HOLDING DEVICE FOR FILLING A SYRINGE WITH A RADIOACTIVE SOLUTION

(71) Applicant: JUBILANT DRAXIMAGE INC., Kirkland (CA)

(72) Inventor: Michael Gertsenchtein, Kanata (CA)

(73) Assignee: JUBILANT DRAXIMAGE INC., Kirkland (CA)

( * ) Notice: Subject to any disclaimer, the term of this patent is extended or adjusted under 35 U.S.C. 154(b) by 291 days.

(21) Appl. No.: 16/825,952

(22) Filed: Mar. 20, 2020

(65) Prior Publication Data

US 2021/0290846 A1    Sep. 23, 2021

(51) Int. Cl.
*A61M 5/178* (2006.01)
*A61M 5/31* (2006.01)
*A61M 5/315* (2006.01)

(52) U.S. Cl.
CPC ........ *A61M 5/1785* (2013.01); *A61M 5/1782* (2013.01); *A61M 5/3129* (2013.01); *A61M 5/31576* (2013.01); *A61M 2005/3126* (2013.01)

(58) Field of Classification Search
CPC .............. A61M 5/1785; A61M 5/1782; A61M 5/3129; A61M 5/31576; A61M 2005/3126
See application file for complete search history.

(56) References Cited

U.S. PATENT DOCUMENTS

| 4,200,804 A * | 4/1980 | Farella ................ A61M 5/1785 250/506.1 |
| 4,401,108 A * | 8/1983 | Galkin .................. A61B 6/107 604/117 |
| 2017/0290987 A1* | 10/2017 | Mandaroux ....... A61M 5/31505 |
| 2019/0080808 A1* | 3/2019 | Schreuder ................ G21G 4/08 |

* cited by examiner

*Primary Examiner* — Dung T Ulsh
(74) *Attorney, Agent, or Firm* — Lavery, De Billy, LLP; Gonzalo Lavin (57) ABSTRACT

Syringe shield for using a syringe that includes a barrel, a tip and a plunger when manipulating a radioactive solution. The syringe shield includes: a shield body in which the syringe is insertable, the shield body having a window; a first flange at a first open end of the syringe shield; a second flange at a second open end of the syringe shield; wherein the second flange, the shield body, and the window include radiation shielding material, and wherein the tip of the syringe is accessible by the second open end of the syringe shield and the plunger extends outside the first open end when the syringe is inserted in the syringe shield.

17 Claims, 14 Drawing Sheets

FIG_4

SHIELDED SYRINGE HOLDING DEVICE FOR FILLING A SYRINGE WITH A RADIOACTIVE SOLUTION

FIELD OF THE INVENTION

The present invention relates to a syringe shield, and more particularly to a shielded syringe holding device for filling a syringe with a radioactive solution.

BACKGROUND OF THE INVENTION

Radioactive drugs, such as metaiodobenzylguanidine (MIBG) combined with radioactive iodine (I-131), are often used in the treatments of cancers and other such afflictions. Typically, these drugs are produced in a specialty pharmacy, packaged in syringes, then transported to medical facilities so that they can be administered to a patient in need. While effective, these drugs pose numerous dangers to various personnel responsible for its fabrication, transportation, handling and usage.

In particular, the medical professionals responsible for filling syringes with these drugs are at risk of exposure to radioactivity, which may be hazardous for their health. As such, it is essential that the syringes, while they are being filled with these radioactive drugs, are covered by a shielded syringe holding device fabricated from a material that prevents excessive radioactivity from escaping the syringe to the surrounding environment.

While various syringe shields currently exist, they are typically sized to house syringes for low volumetric capacities such as 10 mL or 12 mL. There is a need for syringe shields that can house a syringe containing a full dose of the radioactive drug and that is still is easy to manipulate.

In addition, current syringe shields used when syringes are filled with radioactive drugs typically cover the barrel of the syringe and leave the tip of the syringe accessible for manipulation without additional barrier. As a result, the user will be exposed to the radiation emitted therefrom. Furthermore, current syringe shields used when syringes are filled with radioactive drugs comprise complicated mechanical means to secure the syringe to the shield. This complicates the process of filling the syringe, thereby making it more difficult for the user to safely fill the syringe.

There is a need to ease the use of such syringe shields and to better protect the users.

SUMMARY OF THE INVENTION

According to the present invention, there is provided a syringe shield for using a syringe that comprises a barrel, a tip and a plunger when manipulating a radioactive solution, comprising: a shield body in which the syringe is insertable, the shield body comprising a window; a first flange at a first open end of the syringe shield; a second flange at a second open end of the syringe shield; wherein the second flange, the shield body, and the window comprise radiation shielding material, and wherein the tip of the syringe is accessible by the second open end of the syringe shield and the plunger extends outside the first open end when the syringe is inserted in the syringe shield.

DETAILED DESCRIPTION

Based on the aforementioned drawbacks, it is an object of the present invention to provide a syringe shield that limits exposure to radioactivity while a user is filling a syringe with a radioactive solution, or while manipulating a radioactive solution. Manipulating a radioactive solution includes drawing the solution in the syringe and/or expulsing the solution out the syringe.

It is yet another object of the present invention to provide a syringe shield large enough to house a syringe containing a complete dosage of a radioactive solution for a given treatment.

In order to address the above and other drawbacks, a syringe shield is provided.

The present invention is illustrated in further details by the following non-limiting examples.

Referring to FIGS. 1-5, there is shown an embodiment of the syringe shield 2 of the present invention. The syringe shield 2 includes:
  a shield body 4 in which a syringe is insertable, the shield body 4 comprising a window 6, which is preferably on a side thereof,
  a first flange 8 at a first open end 10 of the syringe shield 2,
  a second flange 12 at a second open end 14 of the syringe shield 2,
  wherein the second flange 12, the shield body 4, and the window 6 comprise radiation shielding material.

Figure 1:
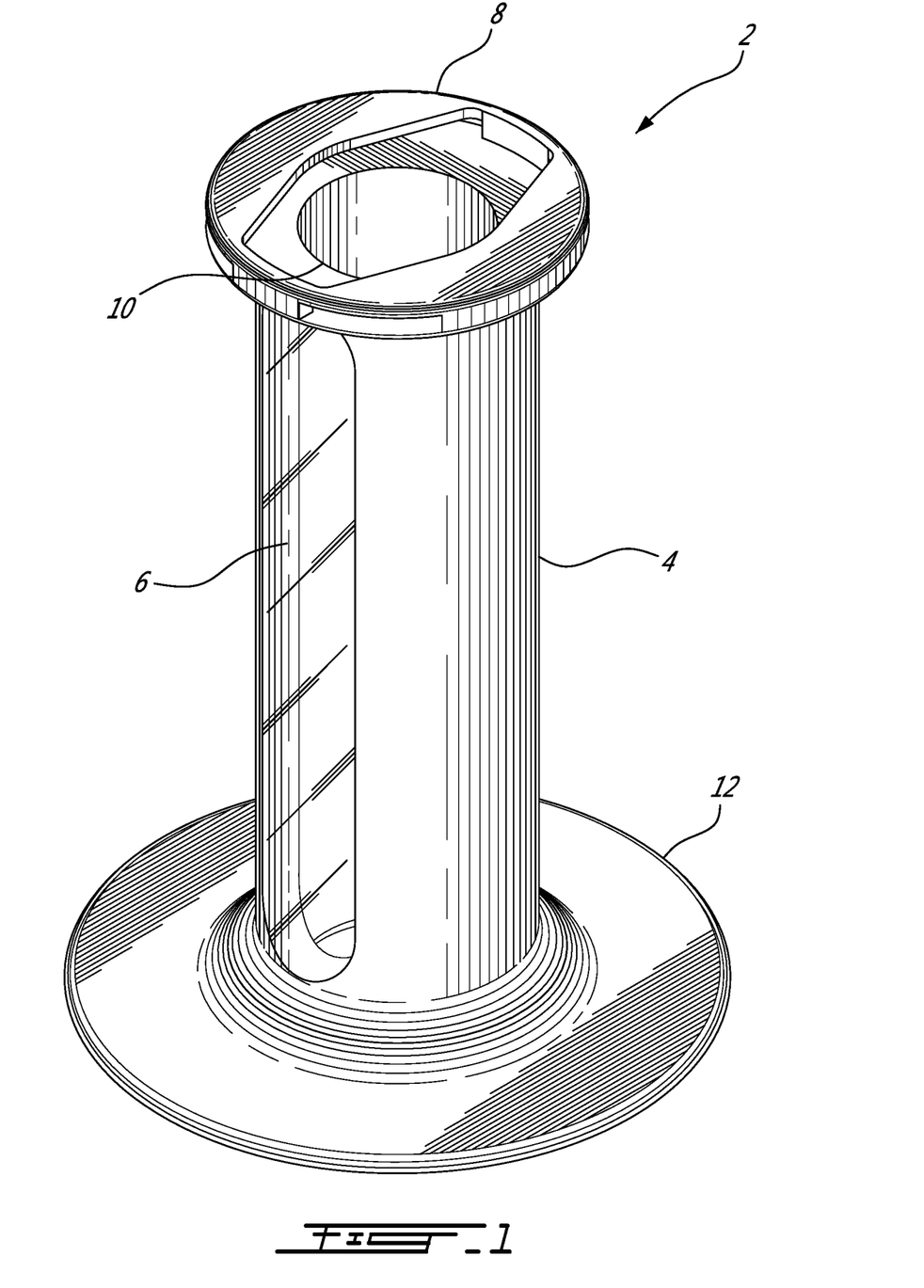
FIG. 1 shows a perspective view of a syringe shield according to an embodiment of the present invention.
Figure 2:
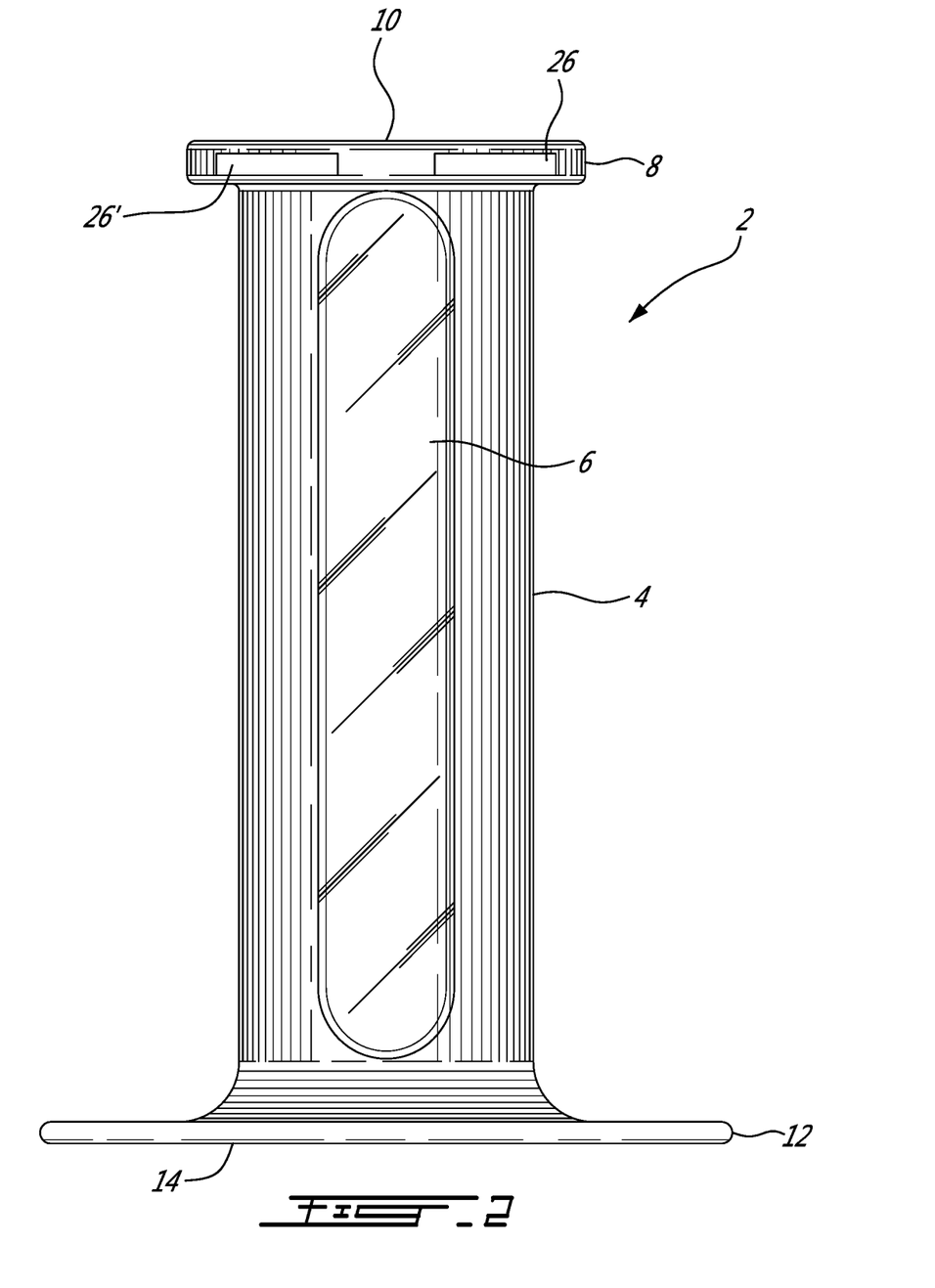
FIG. 2 shows a front view of the syringe shield of FIG. 1.
Figure 3:
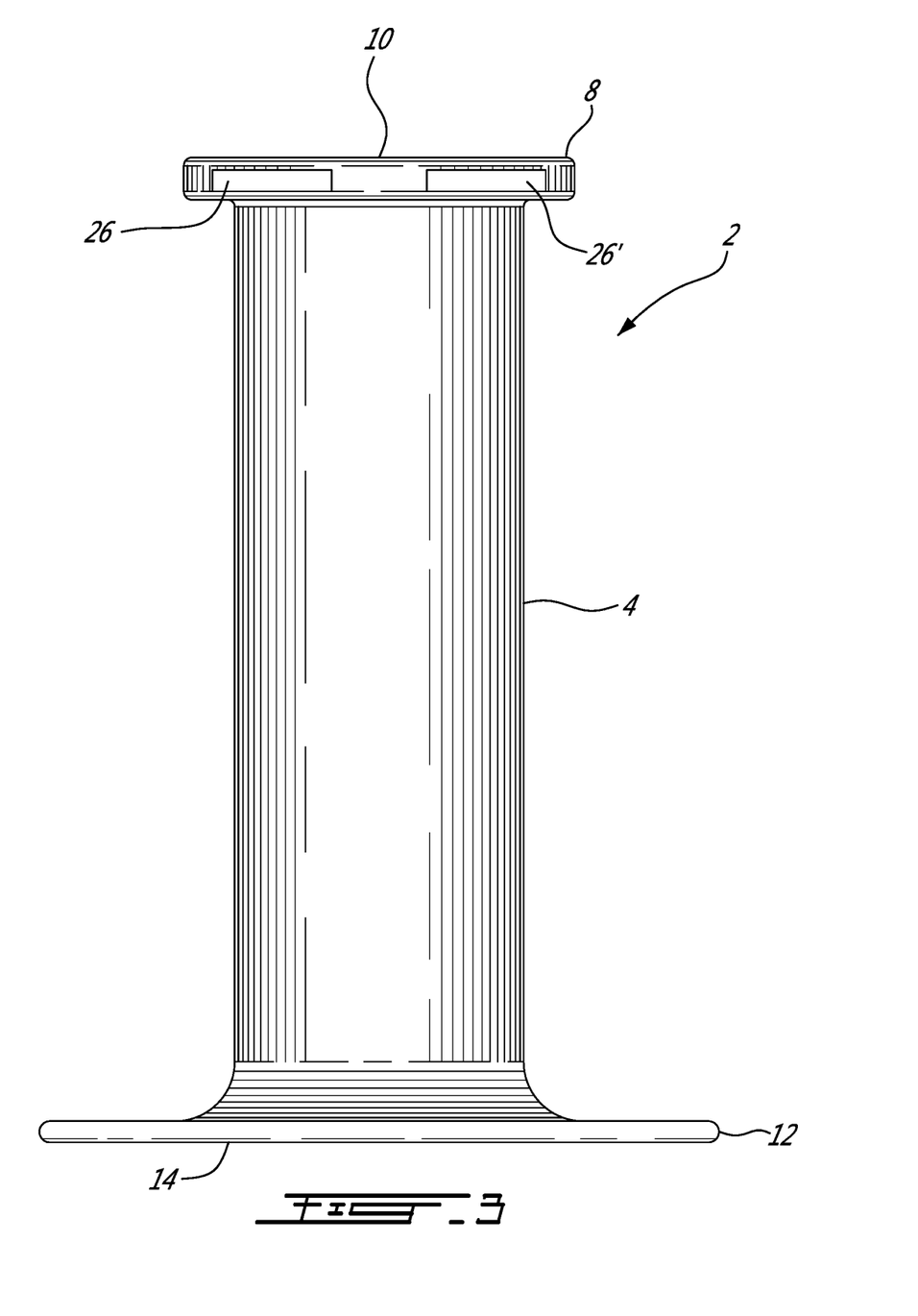
FIG. 3 shows a back view of the syringe shield of FIG. 1.
Figure 4:
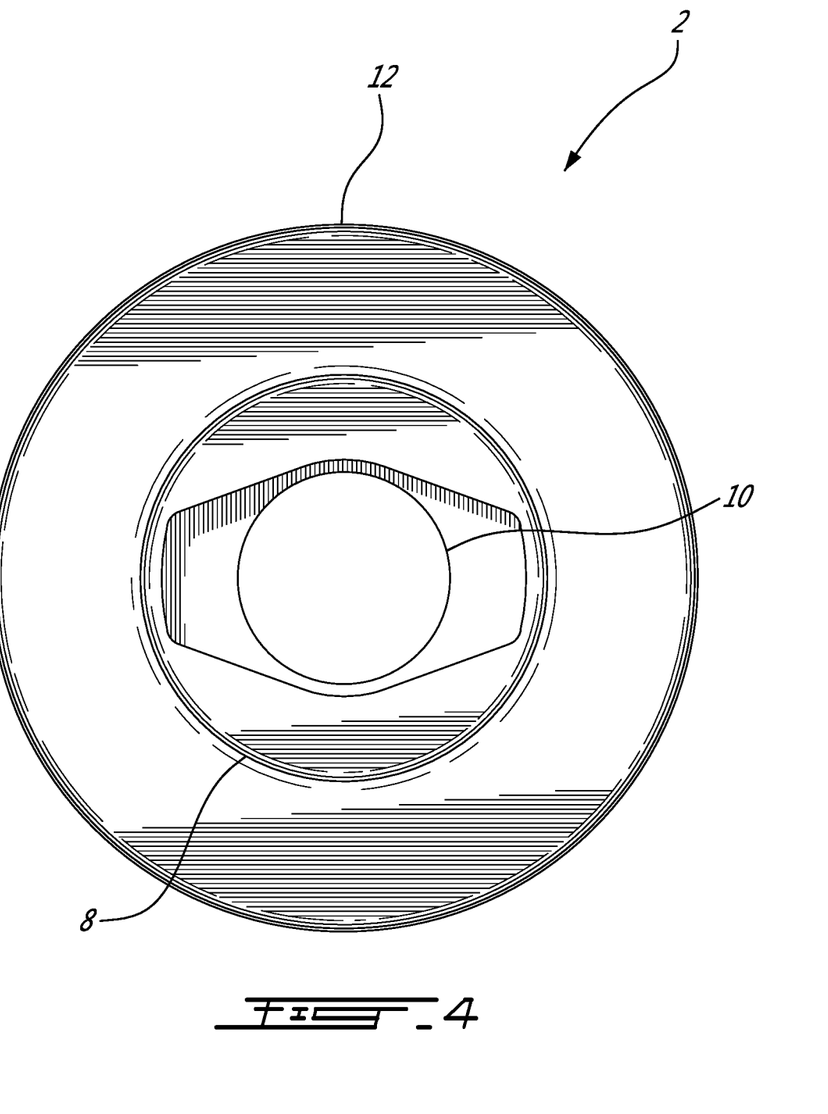
FIG. 4 shows a top view of the syringe shield of FIG. 1.
Figure 5:
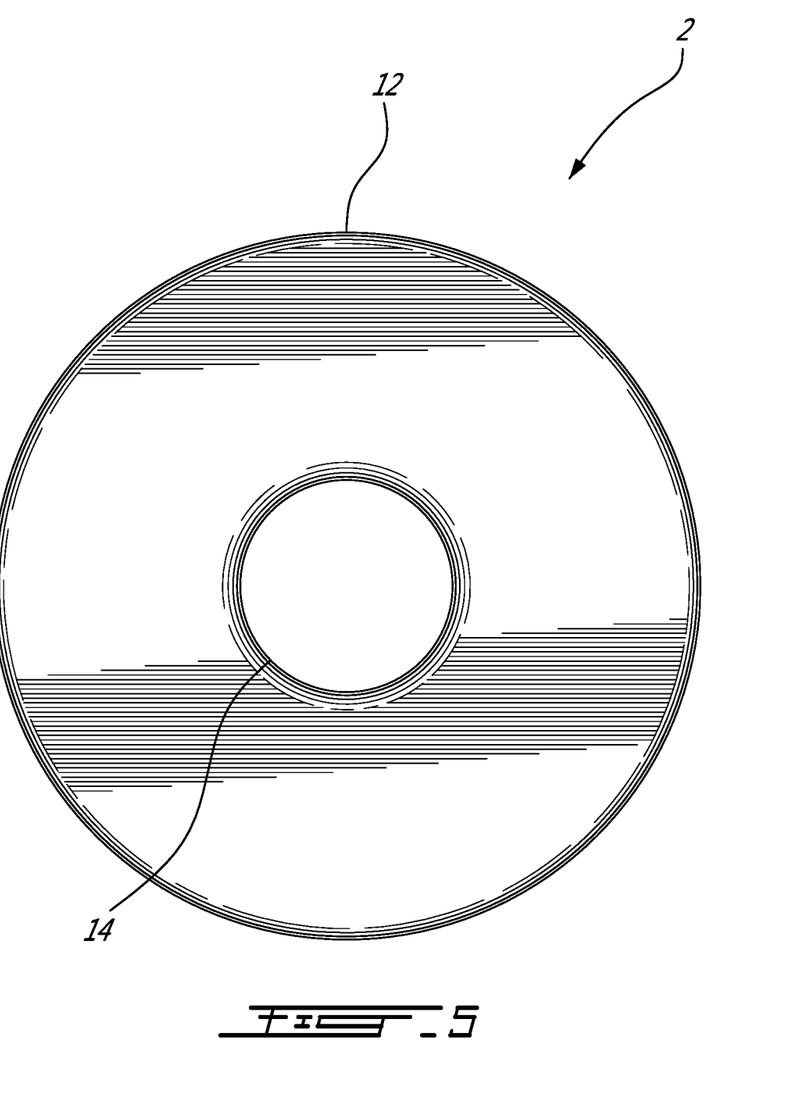
FIG. 5 shows a bottom view of the syringe shield of FIG. 1.
Figure 6:
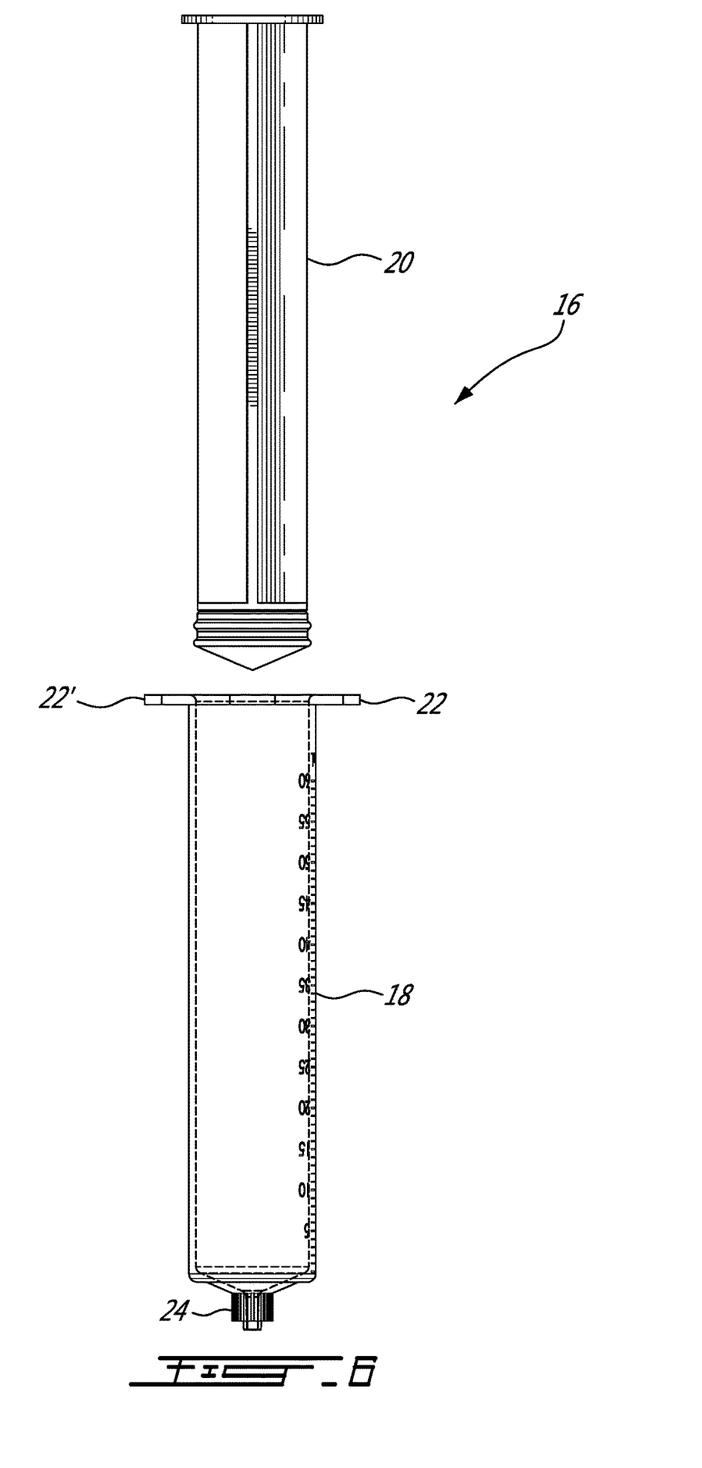
FIG. 6 shows a side view of a syringe which can be used with the syringe shield of the present invention.
Figure 7:
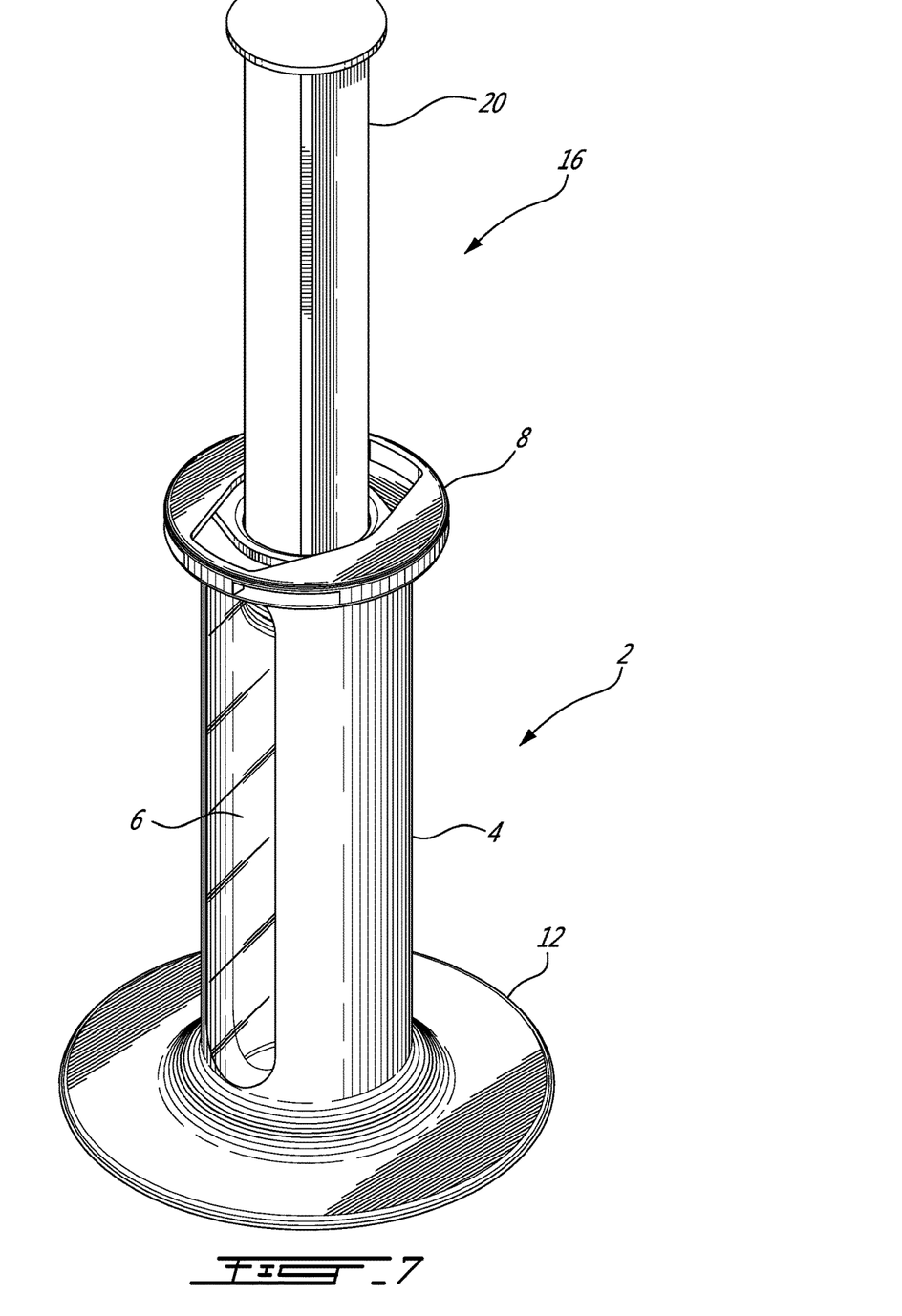
FIG. 7 shows a perspective view of the syringe shield of FIG. 1 with the syringe of FIG. 6 inserted therein.
Figure 8:
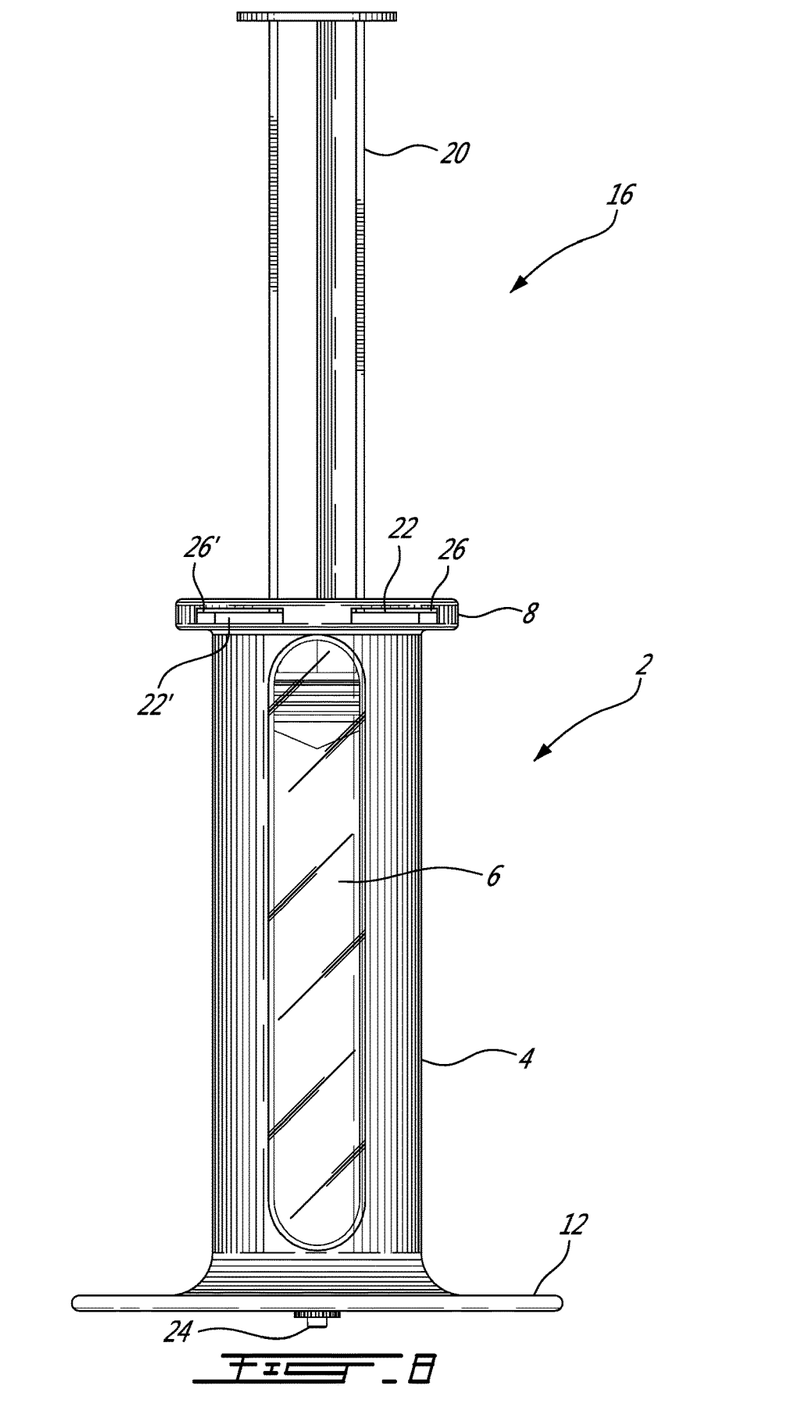
FIG. 8 shows a front view of the syringe shield and syringe of FIG. 7.

The syringe shield 2 of the present invention is for housing a syringe 16 and manipulating a radioactive solution with the syringe 16, such as shown in FIG. 6. Referring to FIG. 6, there is shown a syringe 16 comprising a barrel 18 containing a radioactive solution and comprising a flange 22, 22', and a tip 24.

In embodiments, the syringe shield 2 of the present invention is intended for use with a syringe 16 that is being filled with a radioactive material. For example, a pharmacist may use the syringe shield 2 to house a syringe 16 while filling said syringe 16 with radioactive material before the filled syringe is transported to a hospital for use on a patient.

The shield body 4 is intended to house the barrel 18 of the syringe 16. Accordingly, the shield body 4 comprises a radiation shielding material.

Figure 9:
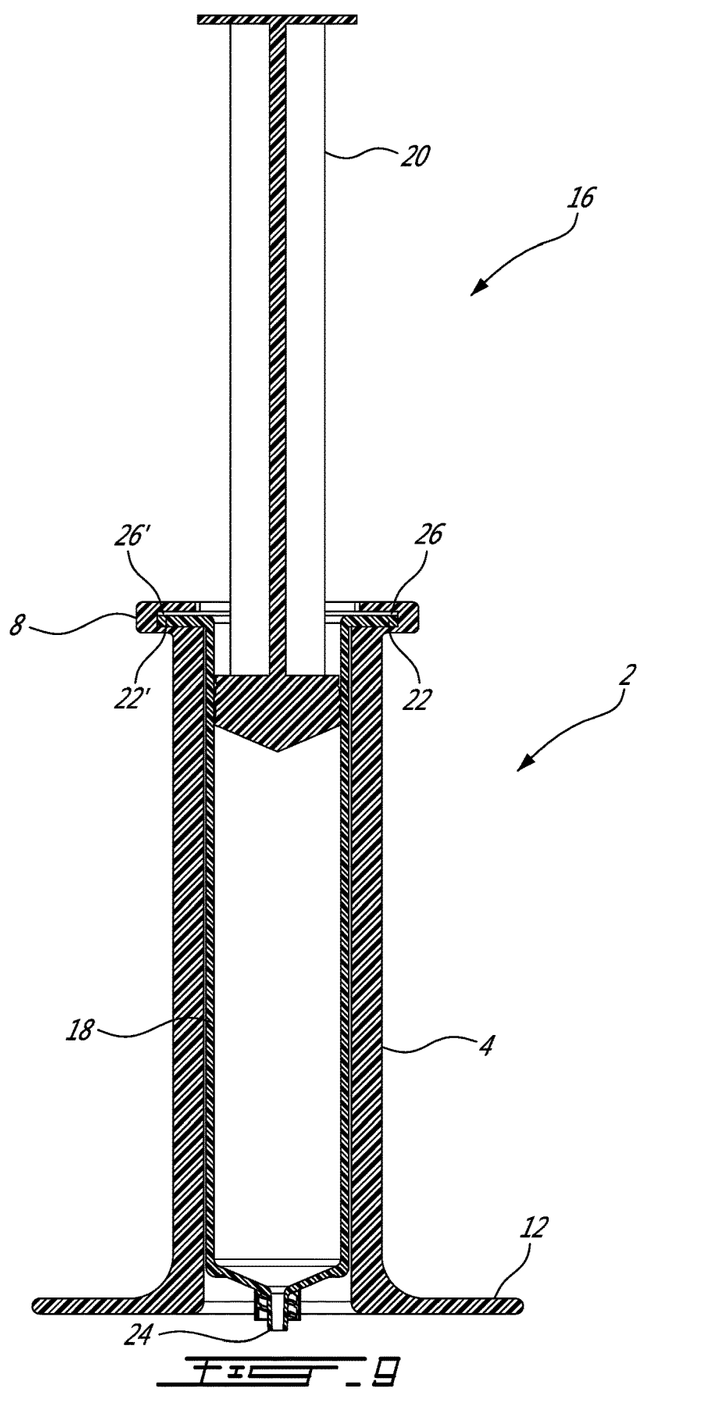
FIG. 9 shows a cross-sectional front view of the syringe shield and syringe of FIG. 7.
Figure 10:
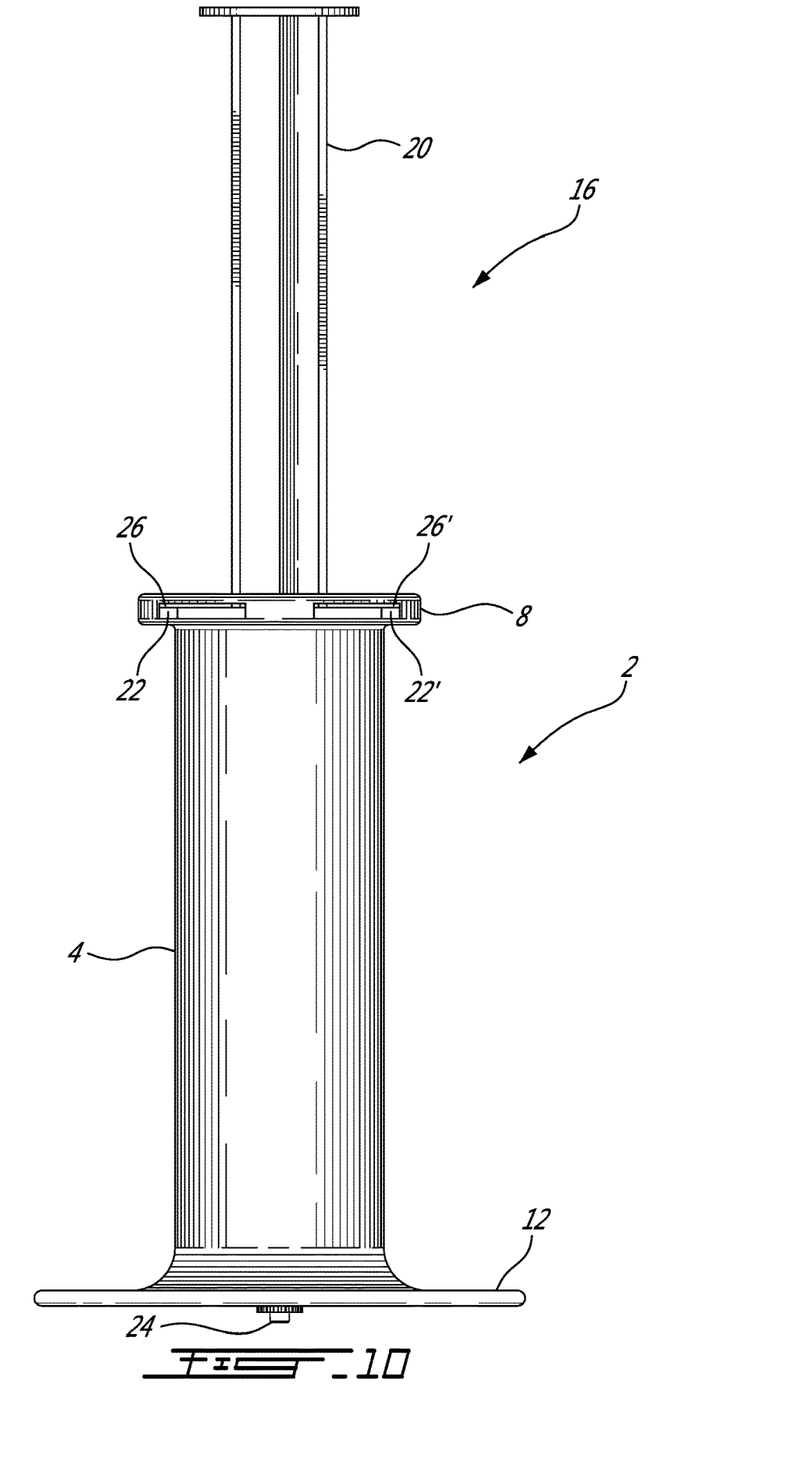
FIG. 10 shows a back view of the syringe shield and syringe of FIG. 7.
Figure 11:
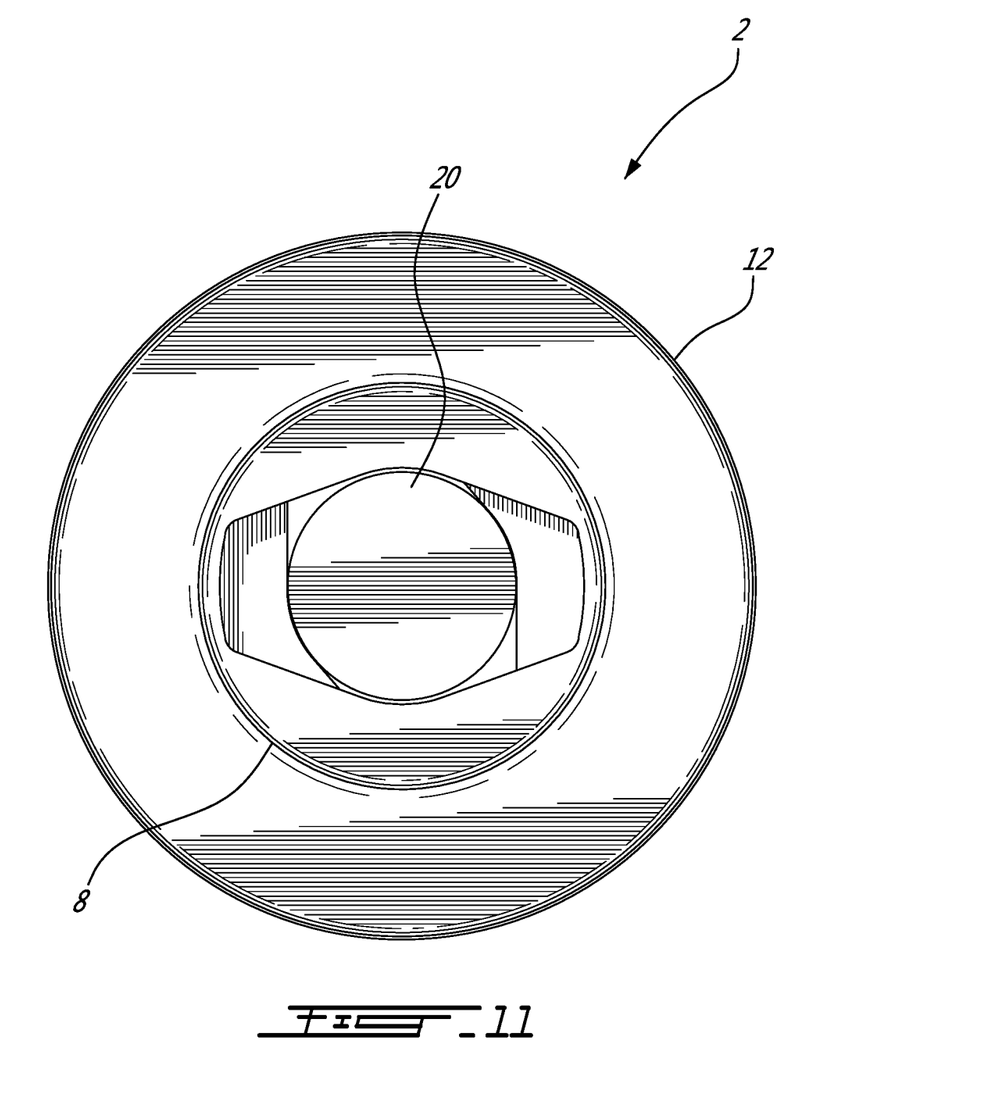
FIG. 11 shows a top view of the syringe shield and syringe of FIG. 7.
Figure 12:
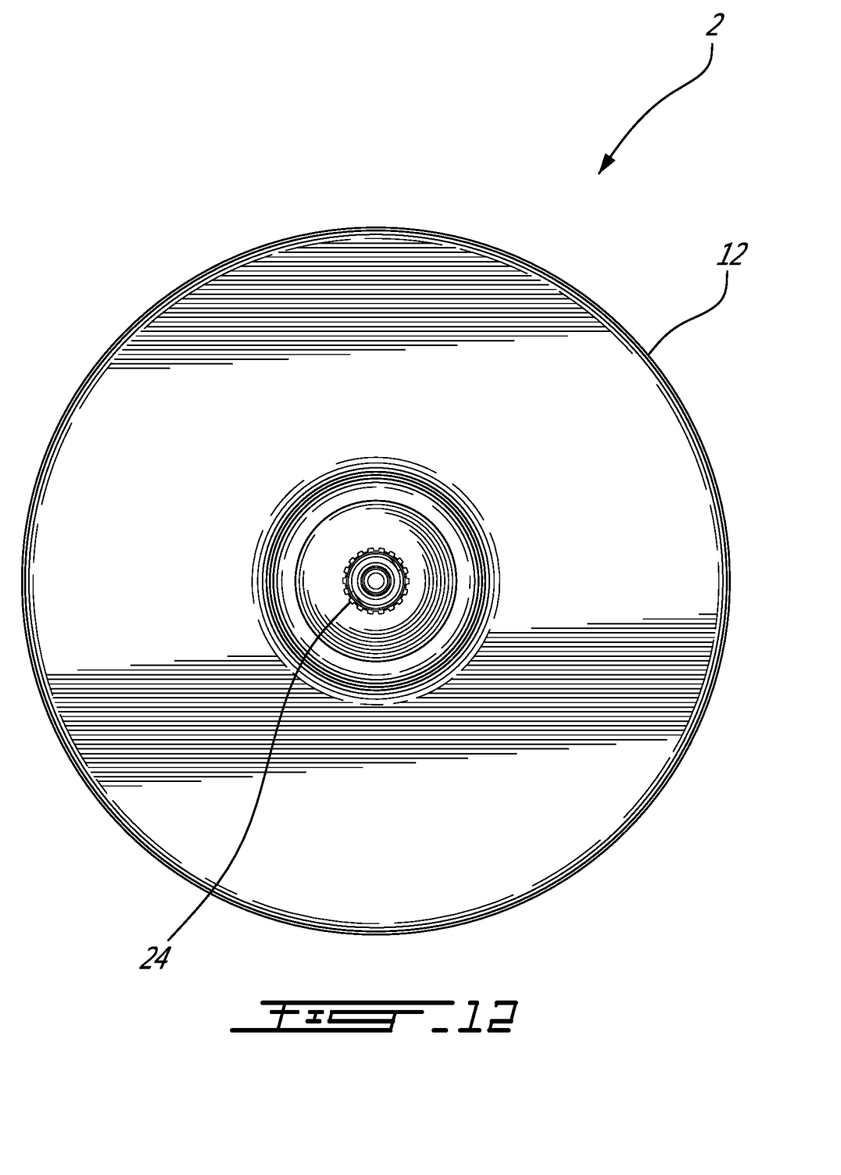
FIG. 12 shows a bottom view of the syringe shield and syringe of FIG. 7.

In embodiments, the syringe shield 2 will be held by the user while the user is filling the syringe 16. Accordingly, in embodiments, the shield body 4 is of a size and shape that can be grasped by a hand of a user. In preferred embodiments, and as shown for example in FIG. 9, the shield body 4 is in the shape of a cylindrical shell, with an interior diameter that is only slightly larger than the diameter of the syringe 16 that is to be inserted into the syringe shield 2.

In embodiments, the user will hold the syringe shield 2 by grasping the shield body 4 and/or by holding the syringe shield 2 up by the first flange 8. In embodiments, the syringe shield 2 can be held by a device or a tool.

The window 6 on the side of the shield body 4 is intended to allow the user to see how much fluid, and more particularly radioactive solution, is inside the syringe 16. However, in order to lessen the user's exposure to radioactivity, the window 6 is made of a transparent radiation shielding material that is of a sufficient thickness to properly shield the user from radiation, and that is of sufficient transparency to allow the user to observe how much of the fluid is in the syringe 16. In preferred embodiments, the window 6 is made of lead glass. As the window 6 will likely shield radiation less effectively than the rest of the shield body 4, in preferred embodiments, the window 6 will occupy as small a surface area as possible. However, in embodiments, the window 6 is long enough so that the user will see a sufficient portion of the length of the barrel 18 of the syringe 16 to be filled, while still being wide enough so as to allow a user to properly see the barrel 18 of the syringe 16. In a preferred embodiment, the barrel 18 of the syringe 16 comprises graduated marks indicating the volume of fluid contained in the syringe 16, and wherein the window 6 is long enough so that at least 70%, 75%, 80%, 85%, 90% or 95% of the graduated marks on the barrel 18 can be seen through the window 6, and is wide enough so as to allow a user to read said at least 70%, 75%, 80%, 85%, 90%, or 95% of the graduated marks. In a preferred embodiment, the window 6 is long enough so that all the graduated marks on the barrel 18 can be seen through the window 6, and is wide enough so as to allow a user to read said graduated marks.

Referring to FIGS. 7-12, there is shown a syringe shield 2 with a syringe 16 inserted therein. As stated, the syringe shield 2 comprises a first open end 10 and a second open end 14. The syringe 16 is insertable in the shield body 4 such that the plunger 20 is extendable through the first open end 10; and the tip 24 is accessible by the second open end 14 for enabling the user to connect a needle, a luer lock or the like to the tip 24, when needed.

In embodiments, when the syringe 16 is inserted into the syringe shield 2, the barrel 18 of the syringe 16 will be housed by the shield body 4, while the plunger 20 of the syringe 16, when in an extended position, will extend through the first open end 10 of the syringe shield 2, and the tip 24 of the syringe 16 will be accessible by the second open end 14 of the syringe shield 2.

In this configuration, the plunger 20 can move freely from an extended position to a retracted position and vice-versa. In this configuration, the tip 24 can be connected to, for example, a needle, and the plunger 20 can be actuated by being pushed and pulled manually or through a pump. The needle can be inserted into a vial containing a radioactive solution, and the syringe 16 can then be filled with the radioactive solution by pulling the plunger 20 into an extended position until the desired amount of the radioactive solution has entered the syringe 16.

The syringe 16 is insertable through the first open end 10 of the syringe shield 2. In an embodiment, the barrel 18 of the syringe 16 comprises a flange 22, 22', and the first flange 8 of the syringe shield 2 comprises a recess that is shaped to receive the flange 22, 22". As shown for example in FIG. 1, the first flange 8 of the syringe shield 2 can also be shaped to receive the flange 22, 22' of the syringe 16. As shown for example in FIG. 7, the first flange 8 of the syringe shield 2 can also be designed to releasably engage with the flange 22, 22' of the of the syringe 16. For example, the flange 22, 22' can function as a twist-lock element that, when twisted, will be received by twist-lock recesses 26, 26' in the first flange 8 of the syringe shield 2 (as shown for example in FIGS. 7 and 8), thereby helping secure the syringe 16 to the syringe shield 2 while the syringe 16 is being filled. To release the syringe 16, the syringe 16 need only be twisted to disengage the syringe flange 22, 22' from the twist-lock flange receivers 26, 26'. This twist-lock mechanism allows for a simple and easy way of releasably securing the syringe 16 to the syringe shield 2 while the syringe 16 is being filled, as well as a simple and easy way of releasably disengaging the syringe 16 from the syringe shield 2 once the syringe 16 has been filled with the radioactive solution.

By having the first flange 8 of the syringe shield 2 releasably engage with the flange 22, 22', this will prevent the user from having to hold the syringe 16 during the filling process, while also allowing the user to pull or push the plunger 20 when filling or emptying the syringe 16.

In an embodiment, the syringe shield 2 and/or the syringe 16 are configured such that, when the syringe 16 is releasably engaged with the first flange 8, graduated marks indicating the volume of fluid in the syringe 16 are visible in the window 6. This would allow users who are filling the syringe 16 to more easily measure how much radioactive solution is in the syringe 16 as it is being filled or emptied.

Referring to FIGS. 1-6, the syringe shield 2 comprises a second flange 12 at the second open end 14. The second flange 12 protects the user from radiation that is coming from below the syringe shield 2 in a general direction from the second open end 14 to the first open end 10. The second flange 12 may also protect the user from radiation that is emitted from the tip 24 of the syringe 16 without covering the second end (thereby keeping the tip 24 of the syringe 16 accessible to the user). The second flange 12 may also protect the user from radiation emitted by a vial containing a radioactive solution when a needle connected to the tip 24 is inserted into said vial for pulling a radioactive solution therefrom and filling the syringe 16. In general, the larger the diameter of the second flange 12, the better the protection from radiation. The second flange 12 should be sufficiently large so as to protect from as much radiation as possible, while still allowing the user to properly hold and manipulate the shield. It is to be understood that the second flange 12 could be of a variety of shapes and sizes. In preferred embodiments, the second flange 12 has a diameter that is larger than the shield body 4, or larger than the diameter of the first flange 8, or is larger than twice the diameter of the shield body 4.

In an embodiment, the radiation-shielding material provides a proper shielding to the radioactive solution, wherein said radioactive solution has a radioactivity up to 400 mCi, 500 mCi, 600 mCi, 700 mCi, 800 mCi, 900 mCi, or 1 Ci. The term "proper shielding" is intended to designate a shielding that will at least provide the ALARA (as low as reasonably achievable) protection from radiation, whereby the dose of radiation received by a user during the manipulation of a syringe 16 with the syringe shield 2 is acceptable in relation to the weight of the syringe shield 2 and the time it is used. ALARA is a known regulation in the radiopharmaceutical field.

The radiation shielding material may comprise tungsten, lead, stainless steel, aluminum alloy or a combination thereof.

In a preferred embodiment, the radiation-shielding material comprises tungsten. In an embodiment, the radiation-shielding material comprises a combination of lead and tungsten. In an embodiment, the radiation-shielding material comprises a combination of stainless steel and tungsten. In an embodiment, the radiation-shielding material comprises a combination of alloy and tungsten. In an embodiment, the radiation-shielding material comprises a combination of stainless steel, aluminum alloy and tungsten.

In preferred embodiments, the shield body 4, the first flange 8, and the second flange 12 are all made of the same material. In even more preferred embodiments, the shield body 4, the first flange 8, and the second flange 12 are all made of tungsten.

As previously mentioned, in preferred embodiments, the window 6 is made of lead glass.

In an embodiment, the syringe shield 2 is dimensioned to receive a syringe 16 containing up to one of thirty milliliters or sixty milliliters of fluid.

In an embodiment, the total weight of the syringe shield 2 is no more than 5 lbs, 6 lbs, 7 lbs, 8 lbs, 9 lbs, or 10 lbs.

Figure 13:
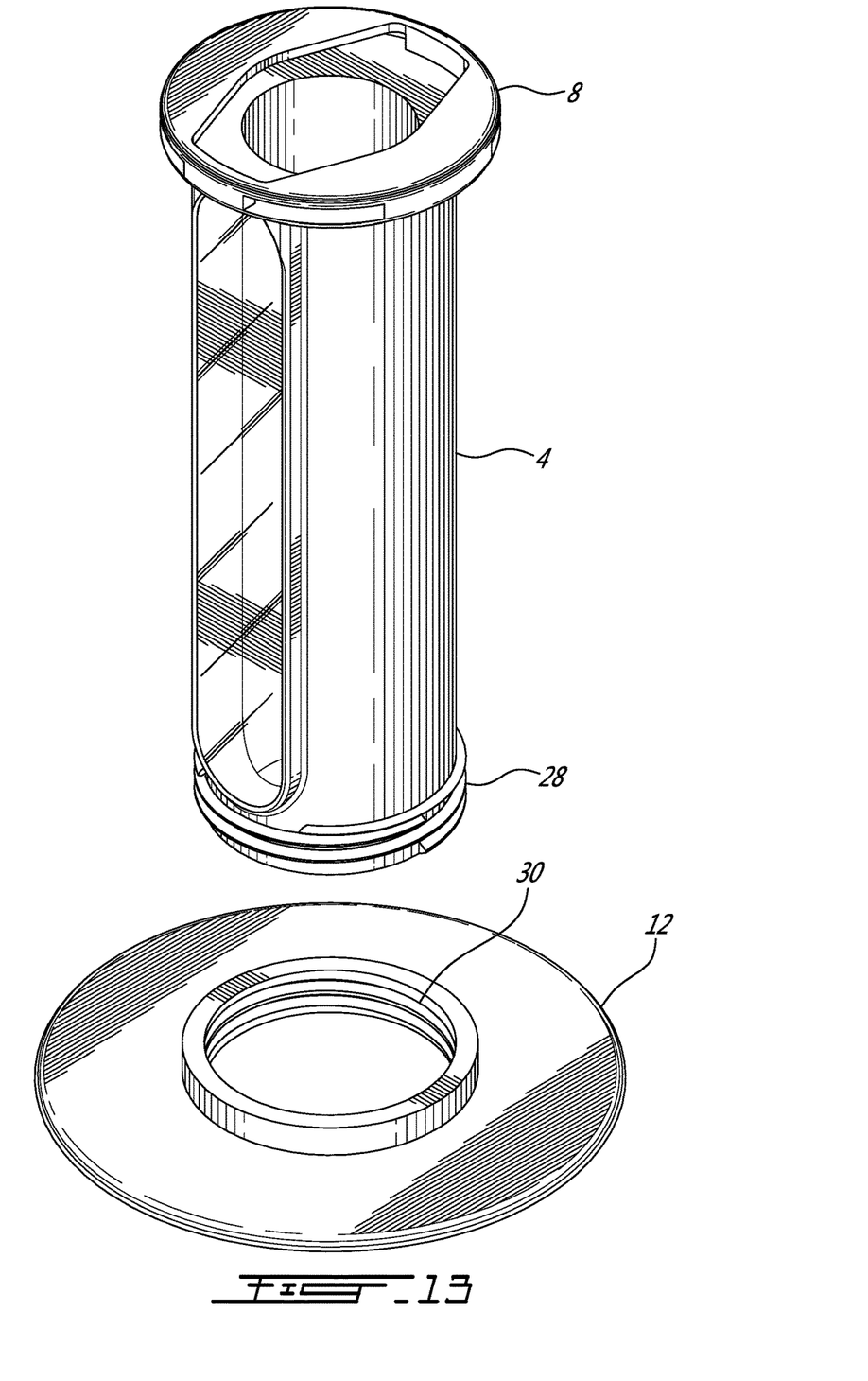
FIG. 13 shows a perspective view of a syringe shield according to another embodiment of the present invention.
Figure 14:
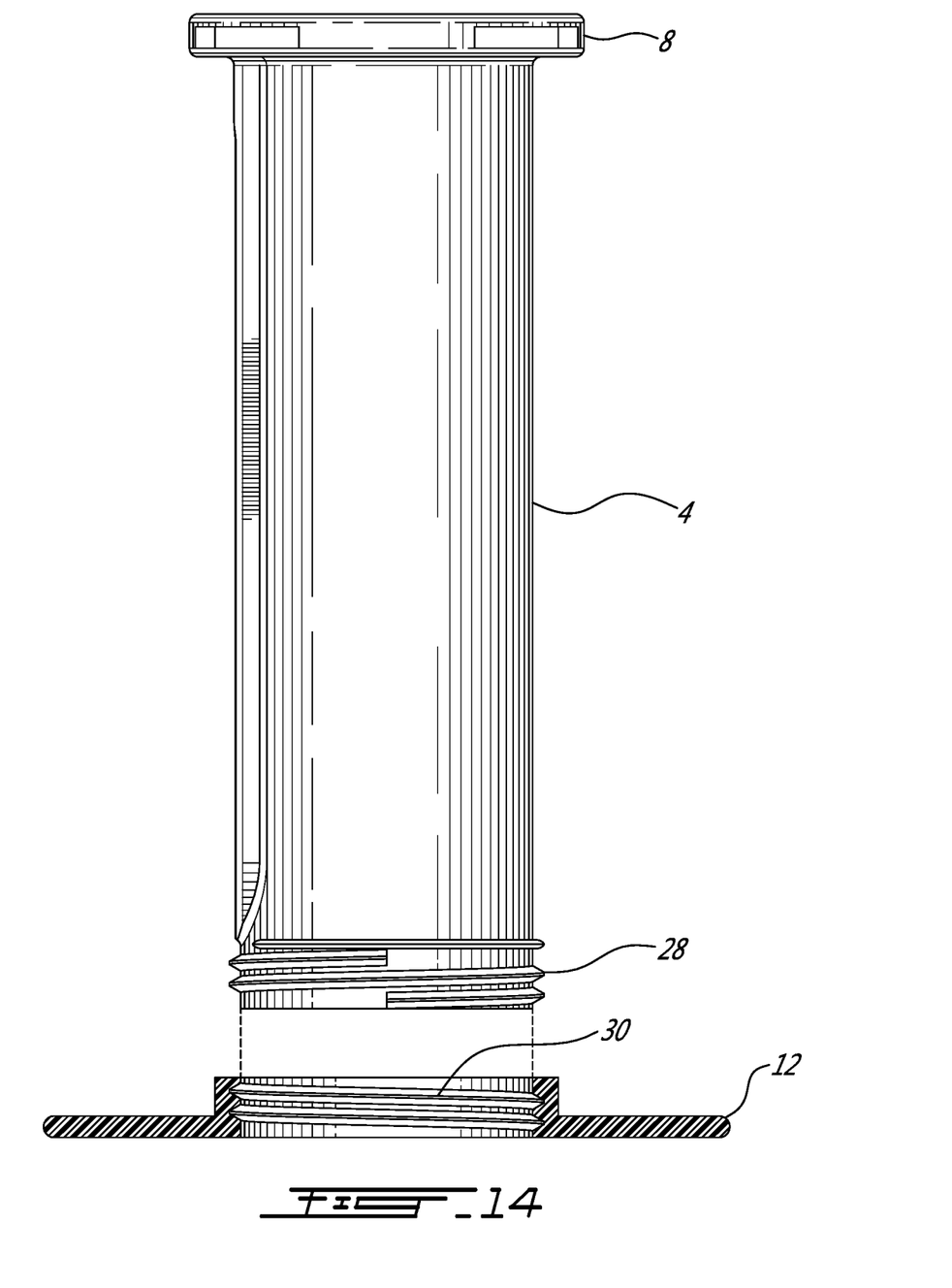
FIG. 14 shows a side partly sectional view of the syringe shield shown in FIG. 13.

In a preferred embodiment that is illustrated for example in FIGS. 13 and 14, the shield body 4 and the first flange 8 are made in one piece; and the second flange 12 is made in a second piece that can be assembled to the shield body 4 and secured in place by any connection mechanisms such as screwing means 28, 30, clips, rivets, or any other connections. In another preferred embodiment, the shield body 4, the first flange 8 and the second flange 12 are made in one piece.

The scope of the claims should not be limited by the preferred embodiments set forth in the examples, but should be given the broadest interpretation consistent with the description as a whole.

The invention claimed is:

1. A syringe shield (2) for using a syringe (16) that comprises a barrel (18), a tip (24) and a plunger (20) when manipulating a radioactive solution, comprising:
   a shield body (4) in which the syringe (16) is insertable, the shield body (4) comprising a window (6) for allowing a user to see a fluid containing the radioactive solution inside the syringe (16);
   a first flange (8) at a first open end (10) of the syringe shield (2);
   a second flange (12) at a second open end (14) of the syringe shield (2);
   wherein the second flange (12), the shield body (4), and the window (6) comprise radiation shielding material,
   wherein the tip (24) of the syringe (16) is accessible by the second open end (14) of the syringe shield (2) and the plunger (20) extends outside the first open end (10) when the syringe (16) is inserted in the syringe shield (2);
   wherein the barrel (18) of the syringe (16) comprises a flange (22, 22');
   wherein the first flange (8) of the syringe shield (2) comprises a recess that is shaped to receive the flange (22, 22');
   wherein the recess in the first flange (8) is designed to releasably engage with the flange (22, 22'); and
   wherein the flange (22, 22') functions as a twist-lock element that, when twisted, will be received by twist-lock recesses (26, 26') in the first flange (8) of the syringe shield (2), thereby helping secure the syringe (16) to the syringe shield (2) while the syringe (16) is being used.

2. The syringe shield (2) of claim 1, wherein the shield body (4) is of a size and shape that can be grasped by a hand of a user.

3. The syringe shield (2) of claim 1, wherein the shield body (4) is in the shape of a cylindrical shell.

4. The syringe shield (2) of claim 1, wherein the shield body (4) is in the shape of a cylindrical shell with an interior diameter that is only slightly larger than a diameter of the syringe (16) that is to be inserted into the syringe shield (2).

5. The syringe shield (2) of claim 1, wherein the syringe shield is holdable by a user by grasping the shield body (4) and/or by holding the syringe shield (2) up by the first flange (8).

6. The syringe shield (2) of claim 1, wherein the window (6) is made of lead glass.

7. The syringe shield (2) of claim 1, wherein the barrel (18) of the syringe (16) comprises graduated marks indicating the volume of fluid contained in the syringe (16), and wherein the window (6) is long enough so that at least 80% of the graduated marks on the barrel (18) can be seen through the window (6), and is wide enough so as to allow a user to read said at least 80% of the graduated marks.

8. The syringe shield (2) of claim 7, wherein the window (6) is long enough so that all the graduated marks on the barrel (18) can be seen through the window (6), and is wide enough so as to allow a user to read said graduated marks.

9. The syringe shield (2) of claim 1, wherein the second flange (12) has a diameter that is larger than the shield body (4).

10. The syringe shield (2) of claim 9, wherein the second flange (12) has a diameter that is larger than a diameter of the first flange (8).

11. The syringe shield (2) of claim 1, wherein the second flange (12) has a diameter that is larger than twice a diameter of the shield body (4).

12. The syringe shield (2) of claim 1, wherein the radiation-shielding material provides a proper shielding to the radioactive solution, wherein said radioactive solution has a radioactivity up to 1 Ci.

13. The syringe shield (2) of claim 1, wherein the radiation shielding material comprises tungsten, lead, stainless steel, aluminum alloy or a combination thereof.

14. The syringe shield (2) of claim 1, wherein the radiation-shielding material of the second flange (12) and the shield body (4) comprises tungsten.

15. The syringe shield (2) of claim 1, wherein the syringe shield (2) is dimensioned to receive the syringe (16) containing up to one of thirty milliliters or sixty milliliters of a fluid.

16. The syringe shield (2) of claim 1, wherein the shield body (4) and the first flange (8) are made in one piece.

17. The syringe shield (2) of claim 1, wherein the shield body (4), the first flange (8) and the second flange (12) are made in one piece.

* * * * *